(12) United States Patent
Engelhardt

(10) Patent No.: US 6,529,271 B1
(45) Date of Patent: Mar. 4, 2003

(54) METHOD OF FINDING, RECORDING AND EVALUATING OBJECT STRUCTURES

(75) Inventor: Johann Engelhardt, Bad Schoenborn (DE)

(73) Assignee: Leica Microsystems Heidelberg GmbH, Heidelberg (DE)

(*) Notice: Subject to any disclaimer, the term of this patent is extended or adjusted under 35 U.S.C. 154(b) by 0 days.

(21) Appl. No.: 09/467,801

(22) Filed: Dec. 20, 1999

(30) Foreign Application Priority Data

Dec. 18, 1998 (DE) .......................................... 198 58 456

(51) Int. Cl.⁷ .......................... G01N 21/64; G02B 21/00
(52) U.S. Cl. ........................ 356/317; 356/417; 356/614; 250/458.1
(58) Field of Search ................................ 356/317, 318, 356/417, 614; 250/458.1, 459.1, 461.1, 461.2

(56) References Cited

U.S. PATENT DOCUMENTS

| | | | |
|---|---|---|---|
| 5,043,570 A | 8/1991 | Takabayashi | 250/216 |
| 5,091,652 A | 2/1992 | Mathies et al. | 250/458.1 |
| 5,587,832 A | 12/1996 | Krause | 359/385 |
| 5,631,734 A | 5/1997 | Stern et al. | 356/317 |

FOREIGN PATENT DOCUMENTS

| | | |
|---|---|---|
| EP | 0 408 035 A2 | 1/1991 |
| EP | 0 440 342 B1 | 7/1996 |
| WO | WO 98/07022 | 2/1998 |

*Primary Examiner*—F. L. Evans
(74) *Attorney, Agent, or Firm*—Foley & Lardner

(57) ABSTRACT

A method of finding, recording and optionally evaluating object structures, especially on slides, preferably of fluorescent object structures such as gene spots. A microscope with a CCD camera, a scanning microscope or a preferably confocal laser scanning microscope can be used for recording and for the rapid and reliable detection of the object structures, with the image data being recorded using an illumination pattern that is projected into the object plane.

15 Claims, 5 Drawing Sheets

METHOD OF FINDING, RECORDING AND EVALUATING OBJECT STRUCTURES

BACKGROUND OF THE INVENTION

1. Field of the Invention

The invention relates to a method of finding, recording and optionally evaluating object structures, preferably of fluorescent object structures such as gene spots, on slides. A microscope with a CCD camera, a scanning microscope, or a confocal laser scanning microscope can be used for recording.

2. Related Prior Art

In a very wide range of applications, for example in the context of an automatic production process, individual—arbitrary—object structures are localized. It is often necessary for object structures to be found again and to be classified with a predefined reliability.

In conventional techniques in which so-called gene scanners have hitherto been used, slides or fluorescent spots arranged on them and having a diameter on the order of 5 μm and 100 μm are imaged. This may be a conventional microscopic image which is recorded, for example, in conjunction with a CCD camera. Likewise, a scanning microscope or a confocal laser scanning microscope (or "CLSM") may be used. In a confocal laser scanning microscope, the detection technology is preferred because the dynamic range which can be detected is generally higher.

In the process of recording using conventional confocal laser scanning microscopes, images are recorded with a very high positional resolution, so that, for object identification, for example, computer-aided segmentation is subsequently necessary. This is accompanied by a very high expenditure in terms of time and requires a considerable computer capacity. With regard to the detectability, the requirements on the recording and evaluation methods are normally around one molecule per square micrometer ($\mu m^2$) and about one percent (1%).

The gene scanners which are known from practice, as well as the methods which are applied with them are extremely complicated, on account of (1) the data recording which is necessary there with an—unnecessarily—high positional resolution, and (2) the subsequently necessary segmentation, with a high computer outlay on account of the necessary capacity, and which necessitates a considerable outlay on apparatus. In addition, the segmentation of the individual fluorescent objects, which is to be carried out with a computer, is often subject to error, so that the required accuracy of about 1% is not always achieved. To this extent, the methods which have hitherto been known from practice are inadequate.

SUMMARY OF THE INVENTION

In view of the foregoing, an object of the present invention is to provide a method of finding, recording and optionally evaluating object structures, especially on slides, preferably of fluorescent object structures such as gene spots, for example, in which method rapid and adequately reliable detection of the object structures is possible. The detection of the object structures must be efficient, it being intended for a specific evaluation method to permit the accurate, rapid and simultaneously reliable identification and localization of the object structures. In the case of detecting fluorescent gene spots, care must be taken that the saturation of the fluorochromes is limiting for the scanning speed. In any case, account should be taken of the fact that fluorescent objects are only able to emit a limited fluorescence intensity.

The preceding object can be achieved by the features described herein. According to one embodiment, a method of acquiring object structures of an object comprises projecting an illumination pattern onto an object plane where the object is located and detecting an object structure of the object with a microscope having a light source and a detector.

In another embodiment of the present invention, a method of finding, recording and optionally evaluating object structures comprises recording image data using an illumination pattern projected into the object plane. For example, fluorescent object structures on slides—such as gene spots can be recorded using a microscope with a CCD camera, a scanning microscope or a confocal laser scanning microscope, with the image data being recorded using an illumination pattern projected into the object plane.

In yet another embodiment of the present invention, an optical detection device for detecting, recording and evaluating fluorescent object structures of an object includes a confocal laser scanning microscope having a light source and a detector, where the object is located in an object plane of said microscope. The device also includes a first illumination mask for projecting an illumination pattern onto the object, where the first illumination mask is disposed along an illumination beam path of said microscope and preferably (not necessarily) arranged symmetrically to an optical axis of said microscope. The projected illumination pattern on the object generates a back reflection or fluorescence distribution from the object structures. The device includes a first detection mask disposed along a detection beam path of the microscope, where the back reflection or fluorescence distribution from the object structures is detected via the first detection mask. An image data storage unit can be used to store extracted object information from the object structures.

Further features of the invention form the subject matter of the claims and will be explained in more detail, in conjunction with further advantages of the invention, with reference to an exemplary embodiment.

BRIEF DESCRIPTION OF THE DRAWINGS

Embodiments of the invention, serving as examples, are illustrated schematically in the drawings, in which.

DETAILED DESCRIPTION OF THE EXEMPLARY EMBODIMENTS

Figure 1:
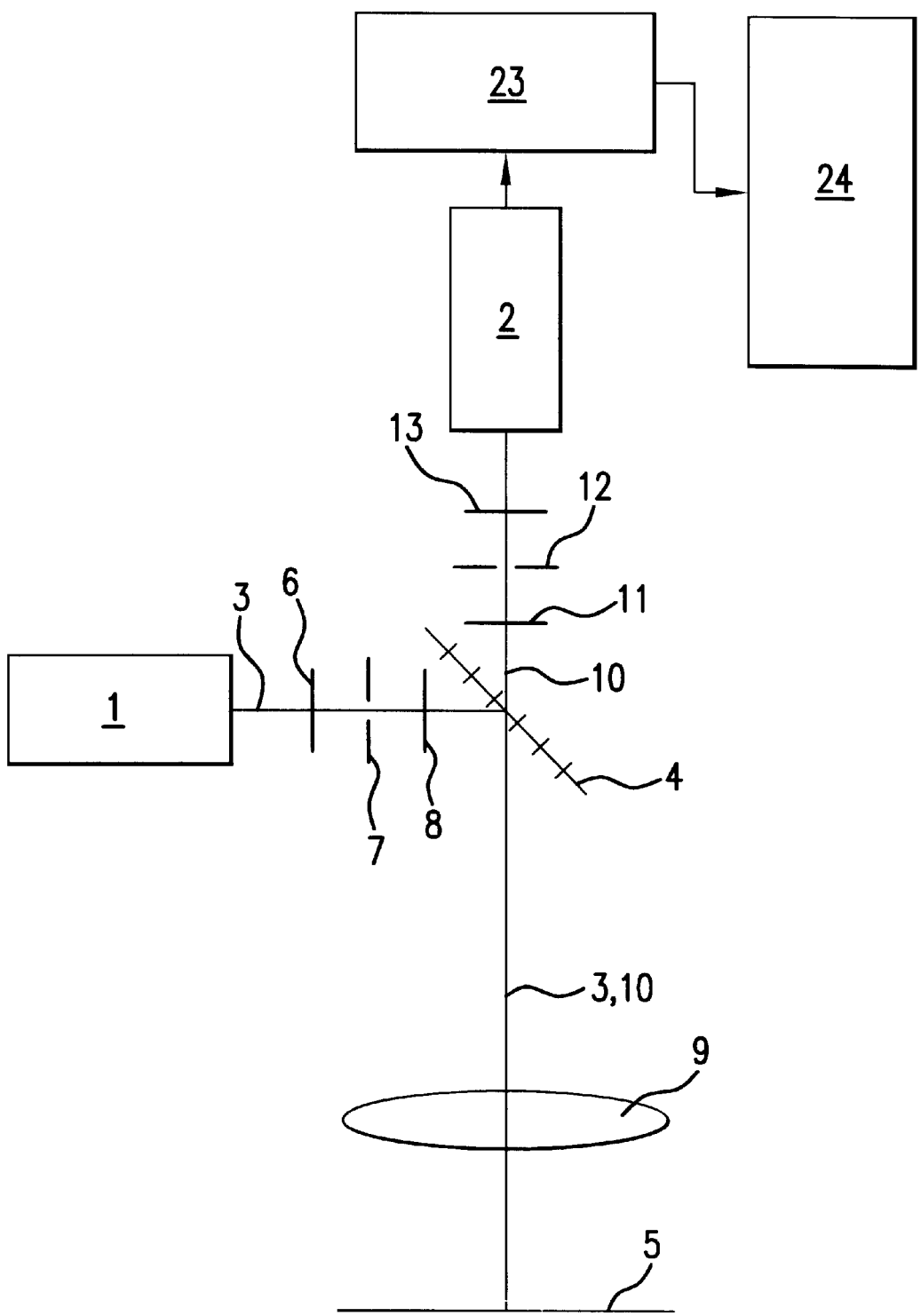
FIG. 1 shows a schematic illustration of the basic construction of an optical arrangement for applying the method of the invention.

According to the invention, it has been recognized that, in order to find, record and also ultimately evaluate object structures, in particular fluorescent object structures—for example gene spots—on slides, it is advantageous if the object structures in the object space are either illuminated with a special illumination pattern or, in the case of fluorescent object structures, excited with a special illumination pattern. This illumination/excitation is implemented by projecting a special illumination mask onto the object structures.

In the manner according to the invention, the slide or the object structures—thus, for example, fluorescent gene spots—can be moved linearly under an illumination pattern. Alternatively, the illumination pattern can be moved linearly over the object structures. During the recording, specific intensity profiles result depending on the position of the object structures in relation to the movement profile of the illumination pattern. These intensity profiles may be described, for example, with a convolution of the illumination pattern with the respective object structures.

Using the shape of the intensity profiles, it is possible to detect quickly and with simple computing routines whether the scan ran centrally or at the edge of the respective object structures. The object structures may be localized without complicated segmentation algorithms: it is possible to calculate the localization of the object structures when the measured intensities of the respective object structures differ from one another. By suitably selecting the boundary conditions, in particular with a predefined arrangement of the object structures and of the object structure sizes, object structure classification and object structure localization can be carried out unequivocally, specifically by a "deconvolution" of the recorded image data with the respective illumination pattern.

The back reflection or the fluorescence in the object space is advantageously excited by using a predefinable illumination pattern. This means that the size and geometry of the illumination pattern can be predefined, in order specifically to be able to perform optimal adaptation to the object structures to be found and recorded.

Furthermore, it is advantageous if the illumination pattern is produced by projecting an illumination mask arranged in the illumination beam path. This illumination mask can be arranged between the light source, for example a laser, and a beam splitter. With respect to an arrangement between the beam splitter and an objective arranged in front of the object plane, it should be considered to take quite specific measures for the unimpeded passage of the back reflection or of the fluorescence light, and also for avoiding the direct detection of that proportion of the illuminating light which is reflected at the illumination mask. In any case, the illumination mask can be arranged symmetrically to the optical axis in the illumination beam path of a microscope, the illuminating light being projected into the object plane or toward the object structure—through the illumination mask—via a lens or a lens system and via the objective. The size and shape of the projected illumination pattern is further advantageously coordinated with the shape and, if appropriate, also the size of the object structure to be detected.

With regard to the illumination of the object structures, it is of further advantage if at least two illumination sources with identical or different illumination masks or one illumination source with a suitable beam splitting means is used, so that more than just one wavelength of the back reflection or more than just one fluorescent colorant can be detected simultaneously. By paralleling at least two illumination sources, the scan speed, in particular, may be increased quite considerably.

According to another embodiment of the present invention, the back reflection or the fluorescence distribution is detected via a detection mask arranged in the detection beam path, the detection mask being further advantageously arranged between the beam splitter and the detector. The pattern of the detection mask is—likewise advantageously—at least largely identical to the pattern of the illumination mask, to this extent agreement with the object structure to be detected also being advantageous.

In the beam scanning embodiment of the invention, the illumination pattern is scanned over the object or over the object structure. In the object scanning embodiment, the object is moved under the stationary light beam. For some applications, object scanning is preferred over beam scanning because the imaging optics can be configured more simply, which in turn results in lower costs.

The object characterization and, if appropriate, determination of the object position can be carried out during the image recording or shortly thereafter. More extensive processing of the image information may follow.

The intensity profiles measured over the object structures during the recording are described in accordance with mathematical "processing", that is to say, for example by convolution of the illumination pattern with the respective object structures. Using suitable computing routines, the shape of the intensity profiles is used to detect whether the scan ran centrally or at the edge of the object structures. In any case, the intensity profiles may be used to determine the actual position of the individual object structures.

Furthermore, it is advantageous that—not least to reduce the outlay on computing and the data to be administered—the information about the object structures recorded is extracted with the aid of mathematical deconvolution of measured image data with the illumination pattern. Here it is possible for the image data to be recorded simultaneously with illuminating light of at least two different wavelengths and to be detectable in at least two different detection channels. The mathematical deconvolution on the respective detection channel is carried out with the corresponding illumination mask, coordination between illumination mask and detection mask being advantageous.

The illumination and detection can advantageously be carried out via at least two illumination and detection masks, it being possible for the individual illumination and detection masks to have different shapes and sizes. On the basis of a predefined shape of the illumination masks—and also of the detection masks—mathematical deconvolution with the aid of special computer hardware is possible. For this purpose, FPGAs (Field Programmable Gate Arrays) can be used, so that processing in real time is possible. In addition, other hardware devices such as digital signal processors (DSPs) and application specific integrated circuits (ASICs) can also be utilized for real time processing. In the ideal case, only the extracted object information from the respective object structures is stored.

A particular advantage of the method according to the invention is to be seen in the fact that data reduction is carried out, which reduces the requirements on the memory or memory demand of the recording and evaluation computer. To this extent, also, the costs of the system are reduced in the manner according to the invention.

The illumination of the object or of the object structures can be carried out with light of a preferably predefinable wavelength, using an essentially circular, rectangular or polygonal illumination mask. As has already been mentioned previously, adaptation of the shape and size of the illumination mask to the respective object structure is advantageous. Furthermore, it is essential that the illumination mask ensures a quasi-homogeneous illumination intensity. In this case, detection is carried out via an essentially circular, rectangular or polygonal detection mask, which can be coordinated with the shape and size of the illumination mask. For data evaluation, it is advantageous to know that the measured intensity signal is the cross-correlation between the illumination pattern and the shape of the object structure—referred to the achievable reflection or fluorescence intensity. This is then the mathematical special case of a convolution. The dimension of the illumination pattern could in this case be greater than the corresponding diffraction-limited Airy disk.

Finally, it should be noted that the object structure may have either microscopic or else macroscopic dimensions. Corresponding coordination of the illumination mask and the detection mask is possible.

By way of one example, application of the method of the present invention can be carried out using the confocal laser scanning microscope arrangement shown in FIG. 1. This arrangement comprises—as essential components—a laser light source 1 and a detector 2. An illumination beam path 3 is deflected toward an object plane 5 by a dichroic beam splitter 4. Arranged in the illumination beam path 3 are a lens system 6, an illumination mask 7, a further lens system 8, the beam splitter 4 and, in front of the object plane 5, an objective 9. Back reflection or the fluorescence light passes from the object plane 5, through the objective 9, over the detection beam path 10, through the beam splitter 4, through a lens system 11 to the detection mask 12 and through the detection mask 12, through a further lens system 13, to the detector 2. The detector 2 can be coupled to a recording and evaluation computer 24, such as a conventional personal computer. A hardware device, such as FPGA 23, can be used for real-time processing of signals from detector 2.

Important components in relation to the method according to the invention are the illumination mask 7 and the detection mask 12, which, according to one embodiment, are coordinated in terms of shape and size, on the one hand with one another and on the other hand with the respective object structures (in the object plane 5), and are arranged in corresponding planes.

Figure 2:
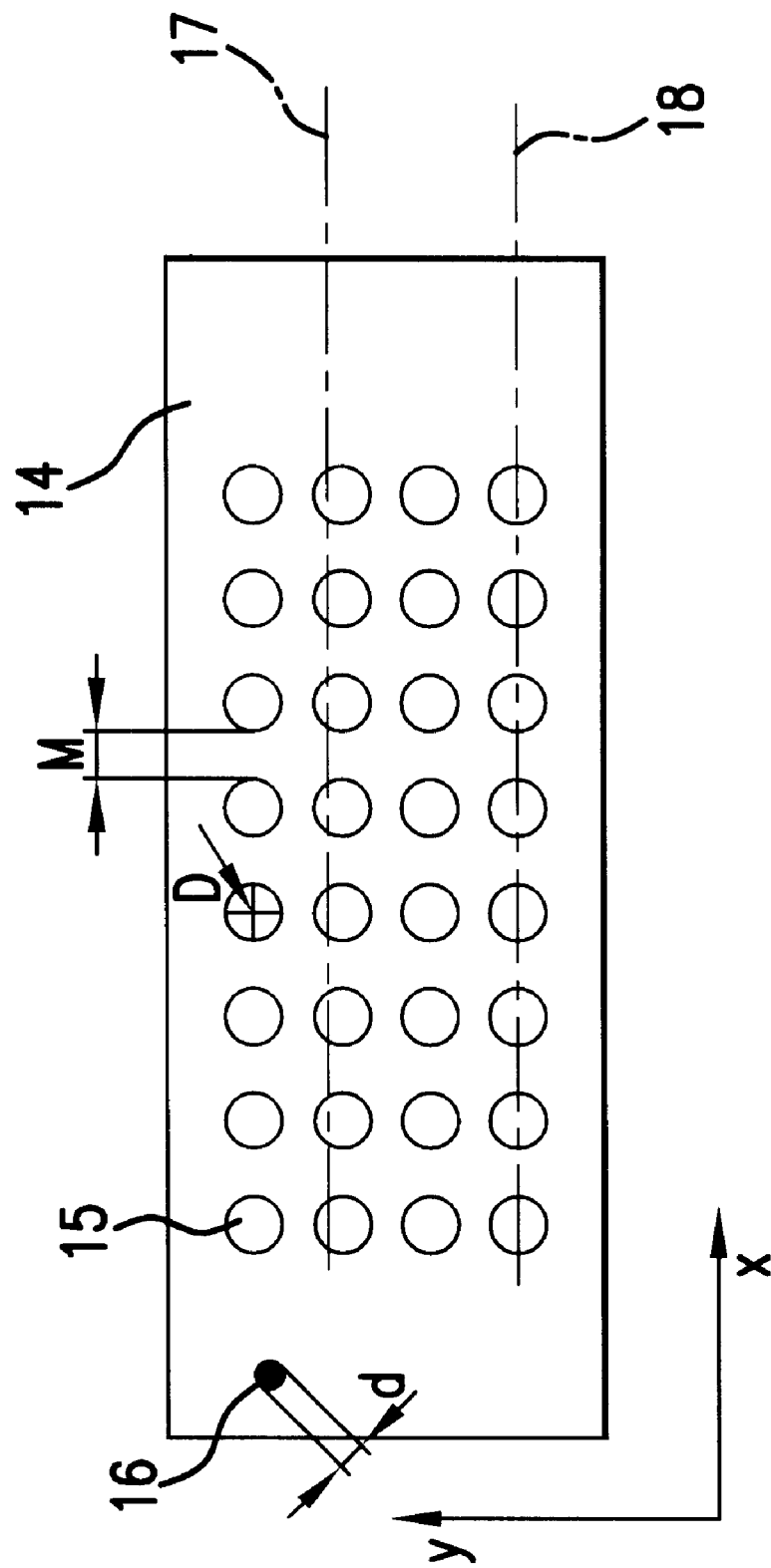
FIG. 2 shows a schematic plan view of a slide with gene spots and an indicated scan path.

FIG. 2 shows, by way of example and in this case schematically, a slide 14 with object structures arranged on it, the latter specifically being gene spots 15. The gene spots 15 shown there are of identical shape and identical size and are arranged equidistantly from one another.

According to one embodiment of the method of the invention, slide 14 is moved under a physical illumination pattern 16 in the x direction along the lines 17, 18, specifically, according to line 17, in the edge region of the respective gene spots 15 and, according to line 18, in the center of the respective gene spots 15.

Figure 3:
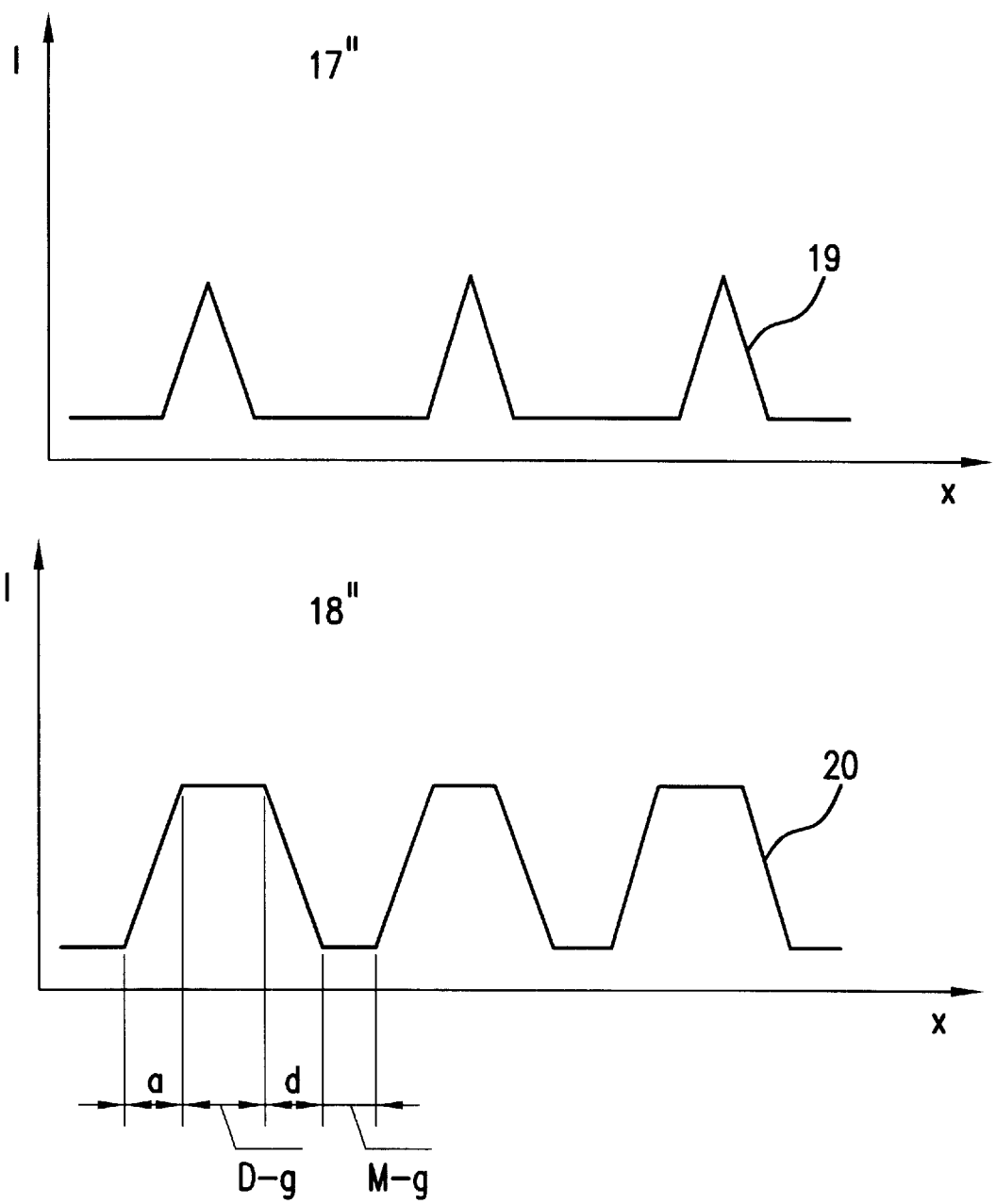
FIG. 3 shows, in two graphs arranged one above another, the intensity profile of the scan movements indicated in FIG. 2.

Scanning produces the measured intensity profiles 19, 20 illustrated in the graphs of FIG. 3, the intensity profile 19 resulting from the scanning operation according to line 17 in FIG. 2, and the intensity profile 20 resulting from the scanning operation according to line 18 from FIG. 2.

The intensity profiles 19, 20 may be described mathematically by means of a convolution of the illumination pattern 16 with the respective gene spots 15. The shape of the intensity profiles 19, 20 makes it possible, by means of simple computing routines, to detect whether the scan ran centrally in accordance with line 18 or at the edge in accordance with line 17 from FIG. 2. The position of the individual gene spots 15 can be determined without complicated segmentation algorithms.

As an addition to the above description, it should be pointed out that the diameter d of the illumination pattern 16, of circular configuration here, the diameter D of the gene spots 15, likewise represented as circular here, and the distance M between two adjacent gene spots 15—measured from edge to edge in the scanning direction—are illustrated in FIG. 2. These parameters are plotted appropriately in FIG. 3, discussed below within the framework of the intensity profiles 19, 20 shown there.

In the intensity profiles 19, 20 shown in FIG. 3, and in the arrangement of the gene spots 15 on the slide 14 selected in FIG. 2, the gene spots have an identical fluorescence intensity. Even if the measured intensities of the gene spots (15) differ from one another, the localization of the gene spots 15 could be calculated using the intensity profile.

The measured intensity profile 20 is illustrated schematically in FIG. 3 (lower graph) under the following assumptions: (1) the illumination pattern 16 has a homogeneous illumination intensity, and (2) the emitted fluorescence intensity of the gene spots 15 is homogeneous.

In the scanning direction (x direction, reference symbol 18 in FIG. 2), the measured signal or the intensity profile 20 rises virtually linearly, to be specific as long as the area of the illumination pattern 16 does not completely overlap the area of the gene spot 15 (left-hand, rising region of the intensity profile, d). As long as the area of the illumination pattern 16 is located completely within the area of the gene spot 15, a constant signal is measured, specifically over a region D-d. As soon as the area of the illumination pattern 16 leaves the area of the gene spot 15 again during the course of scanning, a virtually linearly falling signal is measured (right-hand region of the intensity profile, d). For the period during which the area of the illumination pattern 16 does not exhibit any overlap with the area of a gene spot, no signal is detected (region M-d).

Figure 4:
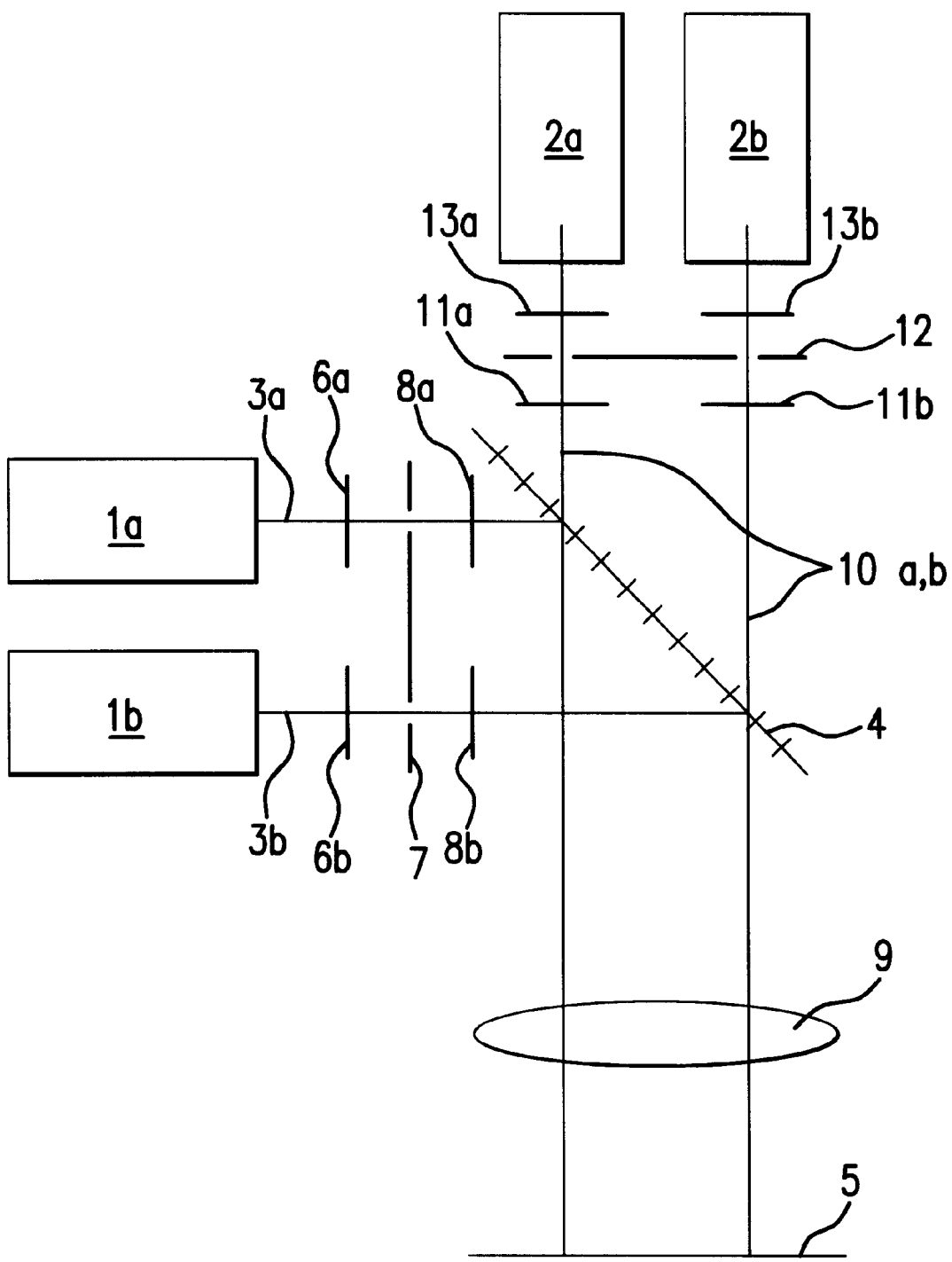
FIG. 4 shows an embodiment of the invention, a schematic illustration of an example optical arrangement utilizing multiple sources and detectors for applying the method according to the invention.

By way of another example, application of the method of the present invention can be carried out using the confocal laser scanning microscope arrangement shown in FIG. 4. This arrangement comprises—as essential components—multiple laser light sources 1a and 1b and multiple detectors 2a and 2b. Illumination beam paths 3a and 3b are deflected toward an object plane 5 by a dichroic beam splitter 4. Arranged in the illumination beam paths 3a and 3b are, respectively, a lens system 6a and 6b, illumination masks 7a and 7b, a further lens system 8a and 8b, the beam splitter 4 and, in front of the object plane 5, an objective 9. Back reflection or the fluorescence light passes from the object plane 5, through the objective 9, over the detection beam paths 10a and 10b, through the beam splitter 4, through a lens system 11a and 11b to the detection mask 12 and through the detection mask 12, through a further lens system 13a and 13b, to the detectors 2a and 2b, respectively. The detectors 2a and 2b can be coupled to a real time hardware device and a recording and evaluation computer, such as described above with reference to FIG. 1. According to this embodiment, the illumination and detection masks can have different shapes and sizes. As mentioned above, by utilizing at least two illumination sources, such as shown in FIG. 4, the scan speed may be increased.

Figure 5:
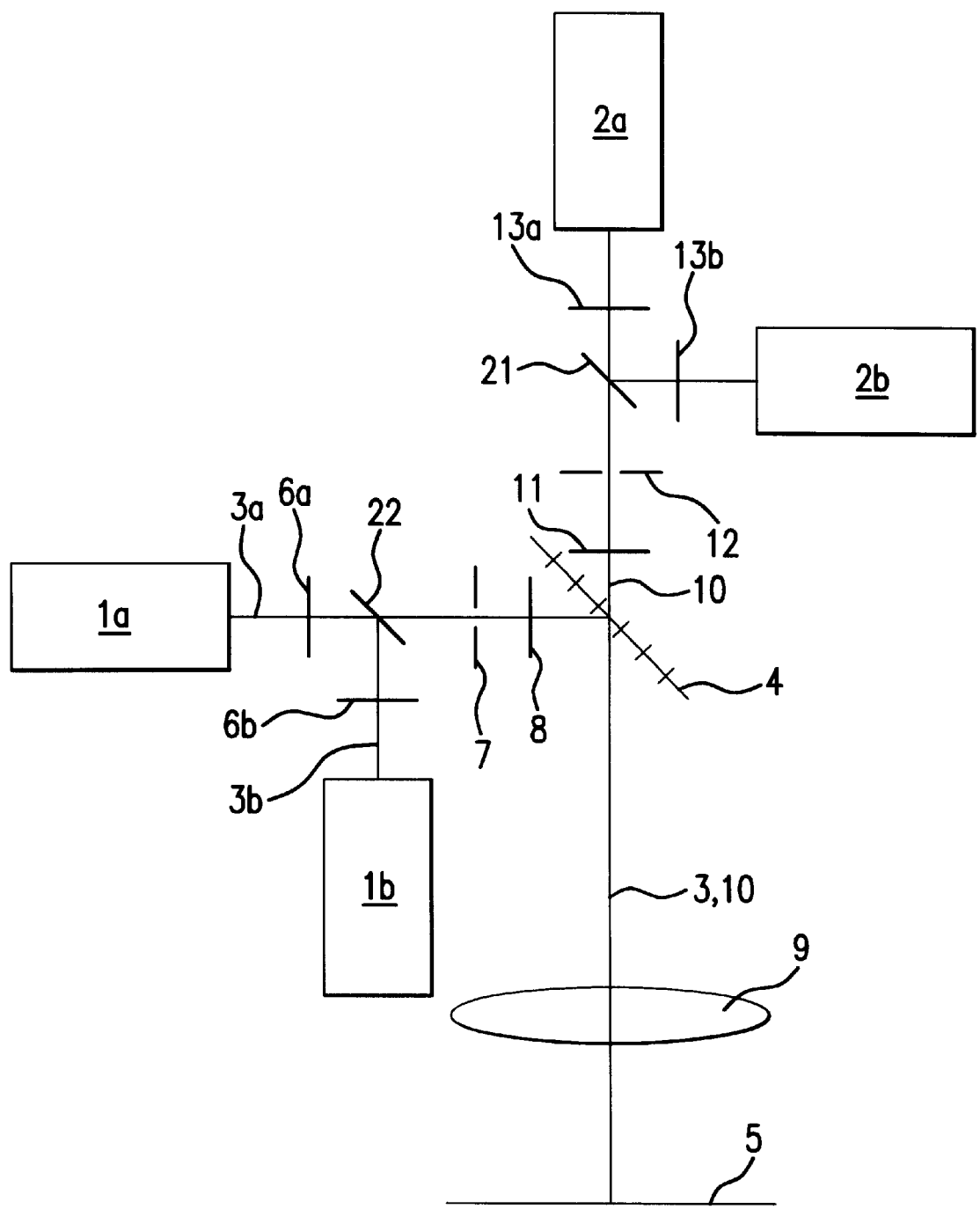
FIG. 5 shows an embodiment of the invention, a schematic illustration of another example optical arrangement utilizing multiple sources and detectors for applying the method of the invention.

Another embodiment of the present invention utilizing multiple sources and detectors is shown in FIG. 5. In this embodiment, a beam recombiner 22 and a dichroic beam splitter 21 can be utilized to respectively propagate and detect at least two different wavelengths along the same illumination and detection paths, 3 and 10, and to allow for multiple detection channels. In this way, more than just one wavelength of the back reflection or more than just one fluorescent colorant can be detected simultaneously.

With regard to further features, which are not specifically illustrated in the figures, reference is made to the general part of the description, in order to avoid repetitions.

Although the invention has been described above by reference to certain embodiments of the invention, the invention is not limited to the embodiments described above. Modifications and variations of the embodiments described above will occur to those skilled in the art, in light of the above teachings. The scope of the invention is defined with reference to the following claims.

German Patent Application No. 198 58 456.3, filed Dec. 18, 1998, including the specification, the drawings, the claims, and the abstract, upon which this application is based, is incorporated herein by reference in its entirety.

What is claimed is:

1. A method of acquiring object structures of an object, comprising:
   projecting an illumination pattern onto an object plane where the object is located;
   detecting an object structure of the object with a microscope having a light source and a detector;
   recording image data corresponding to said object structure with said microscope;
   measuring one or more intensity profiles of said object structure during said recording, wherein said intensity profiles are described mathematically by a convolution of said illumination pattern with said object structure; and
   cross-correlating said illumination pattern and a shape of said object structure to determine said one or more intensity profiles.

2. A method of acquiring object structures of an object, comprising:
   projecting an illumination pattern onto an object plane where the object is located;
   detecting an object structure of the object with a microscope having a light source and a detector;
   recording image data corresponding to said object structure with said microscope;
   measuring one or more intensity profiles of said object structure during said recording, wherein said intensity profiles are described mathematically by a convolution of said illumination pattern with said object structure; and
   determining a position of said object structure.

3. A method of acquiring object structures of an object, comprising:
   projecting more than one illumination pattern onto an object plane where the object is located; and
   detecting an object structure of the object with a microscope having a light source and a detector, wherein at least two illumination sources are used with at least two illumination masks, and wherein an image recording is paralleled using at least two illumination sources.

4. The method according to claim 3, wherein image data is recorded simultaneously with illuminating light of at least two different wavelengths, wherein image data is detected in at least two different detection channels.

5. The method according to claim 4, wherein a mathematical deconvolution on a respective detection channel is carried out with the corresponding illumination mask.

6. The method according to claim 3, further comprising:
   implementing a real time data processing with the aid of a dedicated hardware device, said hardware device selected from the group consisting of a digital signal processor (DSP), a field programmable gate array (FPGA), and an application specific integrated circuit (ASIC), such that only extracted object information from the object structures needs to be stored on a data storage unit coupled to said microscope.

7. A method of finding, recording and evaluating fluorescent gene spots on slides, using a microscope with a CCD camera, a scanning microscope or a confocal laser scanning microscope, wherein image data is recorded using an illumination pattern projected into an object plane, and wherein at least two illumination sources are used with identical or different illumination masks.

8. A method of finding, recording and evaluating fluorescent gene spots on slides, using a microscope with a CCD camera, a scanning microscope or a confocal laser scanning microscope, wherein image data is recorded using an illumination pattern projected into an object plane, and wherein an image recording is paralleled using at least two illumination sources.

9. A method of finding, recording and evaluating fluorescent gene spots on slides, using a microscope with a CCD camera, a scanning microscope or a confocal laser scanning microscope, wherein image data is recorded using an illumination pattern projected into an object plane, and wherein intensity profiles measured over the object structures during the recording are described mathematically by convolution of the illumination pattern with the respective object structures.

10. The method as claimed in claim 9, wherein the shape of the intensity profiles is used, by means of suitable computing routines, to detect whether a scan ran centrally or at the edge of the object structures.

11. The method as claimed in claim 9, wherein the intensity profiles are used to determine the actual position of the individual object structures.

12. A method of finding, recording and evaluating fluorescent gene spots on slides, using a microscope with a CCD camera, a scanning microscope or a confocal laser scanning microscope, wherein image data is recorded using an illumination pattern projected into an object plane, wherein information about the object structures recorded is extracted with the aid of mathematical deconvolution of measured image data with the illumination pattern, and wherein image data is recorded simultaneously with illuminating light of at least two different wavelengths, and can be detected in at least two different detection channels.

13. The method as claimed in claim 12, wherein the mathematical deconvolution on the respective detection channel is carried out with the corresponding illumination mask.

14. A method of finding, recording and evaluating fluorescent gene spots on slides, using a microscope with a CCD camera, a scanning microscope or a confocal laser scanning microscope, wherein image data is recorded using an illumination pattern projected into an object plane, wherein illumination and detection are carried out simultaneously via at least two illumination and detection masks, and wherein individual illumination and detection masks have different shapes and sizes.

15. The method as claimed in claim 14, wherein on the basis of a predefined shape of the illumination masks, a mathematical deconvolution is implemented in real time with the aid of a dedicated hardware device, said hardware device selected from the group consisting of a digital signal processor (DSP), a field programmable gate array (FPGA), and an application specific integrated circuit (ASIC), such that only the extracted object information from the object structures is to be stored.

* * * * *